(12) United States Patent
Liu

(10) Patent No.: US 11,324,567 B2
(45) Date of Patent: May 10, 2022

(54) EXPANDABLE TISSUE CAVITY MARKER DEVICES, SYSTEMS AND DEPLOYMENT METHODS

(71) Applicant: Medtronic Advanced Energy, LLC, Minneapolis, MN (US)

(72) Inventor: Yisi Liu, Winchester, MA (US)

(73) Assignee: MEDTRONIC ADVANCED ENERGY, LLC, Minneapolis, MN (US)

( * ) Notice: Subject to any disclaimer, the term of this patent is extended or adjusted under 35 U.S.C. 154(b) by 605 days.

(21) Appl. No.: 16/033,836

(22) Filed: Jul. 12, 2018

(65) Prior Publication Data

US 2019/0231473 A1    Aug. 1, 2019

Related U.S. Application Data

(60) Provisional application No. 62/624,977, filed on Feb. 1, 2018.

(51) Int. Cl.
*A61B 6/00* (2006.01)
*A61B 90/00* (2016.01)
*A61B 17/00* (2006.01)

(52) U.S. Cl.
CPC .... *A61B 90/39* (2016.02); *A61B 2017/00867* (2013.01); *A61B 2017/00889* (2013.01); *A61B 2017/00898* (2013.01); *A61B 2090/3908* (2016.02); *A61B 2090/3912* (2016.02); *A61B 2090/3966* (2016.02); *A61B 2090/3987* (2016.02)

(58) Field of Classification Search
CPC ..................................................... A61B 90/39
See application file for complete search history.

(56) References Cited

U.S. PATENT DOCUMENTS 3,157,524 A    11/1964  Artandi
3,520,402 A    7/1970   Nichols et al.
4,832,686 A    5/1989   Anderson
(Continued)

OTHER PUBLICATIONS

U.S. Appl. No. 16/033,694, filed Jul. 12, 2018, First named inventor: Yisi Liu.

*Primary Examiner* — Joel F Brutus
(74) *Attorney, Agent, or Firm* — Patterson Thuente Pedersen, P.A.

(57) ABSTRACT

Embodiments relate to expandable tissue cavity markers and corresponding systems and deployment methods. In one embodiment, an expandable tissue cavity marker comprises a pouch and at least one radiopaque marker element. The pouch can transition between a compressed state, in which a profile or dimension of the tissue cavity marker is reduced such that the tissue cavity marker can be deployed through a minimally invasive surgical procedure incision, and an expanded state, in which a profile or dimension of the tissue cavity marker is increased such that the tissue cavity marker fills or defines a volume of a tissue cavity. In one embodiment, the pouch can be transformed between the compressed state and the expanded state by delivery of a fill material into the pouch. The pouch can comprise one or more functional materials in embodiments, including materials that provide an anti-infection, hemostasis, anti-migration, medicinal, or other function to the tissue cavity marker.

31 Claims, 4 Drawing Sheets

(56) References Cited

U.S. PATENT DOCUMENTS

| | | |
|---|---|---|
| 4,957,479 A | 9/1990 | Roemer |
| 5,019,087 A | 5/1991 | Nichols |
| 5,429,582 A | 7/1995 | Williams |
| 5,607,477 A | 3/1997 | Schindler et al. |
| 5,676,146 A | 10/1997 | Scarborough |
| 5,716,404 A | 2/1998 | Vacanti et al. |
| 5,873,865 A | 2/1999 | Horzewski et al. |
| 6,030,333 A | 2/2000 | Sioshansi et al. |
| 6,071,301 A | 6/2000 | Cragg et al. |
| 6,161,034 A | 12/2000 | Burbank et al. |
| 6,228,055 B1 | 5/2001 | Foerster et al. |
| 6,270,464 B1 | 8/2001 | Fulton, III et al. |
| 6,340,367 B1 | 1/2002 | Stinson et al. |
| 6,477,423 B1 | 11/2002 | Jenkins |
| 6,579,310 B1 | 6/2003 | Cox et al. |
| 6,699,205 B2 | 3/2004 | Fulton, III et al. |
| 6,725,083 B1 | 4/2004 | Burbank et al. |
| 7,047,063 B2 | 5/2006 | Burbank et al. |
| 7,229,417 B2 | 6/2007 | Foerster et al. |
| 7,524,274 B2 | 4/2009 | Patrick et al. |
| 7,547,274 B2 | 6/2009 | Rapach et al. |
| 7,875,059 B2 | 1/2011 | Patterson et al. |
| 7,972,261 B2 | 5/2011 | Lamoureux et al. |
| 8,052,658 B2 | 11/2011 | Field |
| 8,060,183 B2 | 11/2011 | Leopold et al. |
| 8,157,862 B2 | 4/2012 | Corbitt, Jr. et al. |
| 8,486,028 B2 | 7/2013 | Field |
| 9,014,787 B2 | 4/2015 | Stubbs et al. |
| 9,199,092 B2 | 12/2015 | Stubbs et al. |
| 9,386,942 B2 | 7/2016 | Chi Sing et al. |
| 9,615,915 B2 | 4/2017 | Lebovic et al. |
| 2001/0034528 A1 | 10/2001 | Foerster et al. |
| 2001/0041936 A1 | 11/2001 | Corbitt, Jr. et al. |
| 2001/0047164 A1 | 11/2001 | Teague et al. |
| 2002/0072806 A1 | 6/2002 | Buskirk et al. |
| 2003/0083732 A1 | 5/2003 | Stinson |
| 2004/0124105 A1* | 7/2004 | Seiler ............... A61B 90/39 206/363 |
| 2004/0249457 A1 | 12/2004 | Smith et al. |
| 2005/0049489 A1 | 3/2005 | Foerster et al. |
| 2005/0074405 A1 | 4/2005 | Williams, III |
| 2005/0080338 A1 | 4/2005 | Sirimanne et al. |
| 2005/0080339 A1 | 4/2005 | Sirimanne et al. |
| 2005/0101860 A1 | 5/2005 | Patrick et al. |
| 2005/0143770 A1 | 6/2005 | Carter et al. |
| 2005/0165480 A1 | 7/2005 | Jordan et al. |
| 2005/0234336 A1* | 10/2005 | Beckman ............... A61B 90/39 600/431 |
| 2006/0025795 A1 | 2/2006 | Chesbrough et al. |
| 2006/0058570 A1 | 3/2006 | Rapach et al. |
| 2006/0116713 A1 | 6/2006 | Sepetka et al. |
| 2006/0173296 A1 | 8/2006 | Miller et al. |
| 2007/0021642 A1 | 1/2007 | Lamoureux et al. |
| 2007/0032703 A1* | 2/2007 | Sankaran ............ A61B 17/3439 600/208 |
| 2007/0038014 A1 | 2/2007 | Cox et al. |
| 2007/0038017 A1 | 2/2007 | Chu |
| 2007/0167668 A1 | 7/2007 | White et al. |
| 2008/0015472 A1 | 1/2008 | Ressemann et al. |
| 2008/0045773 A1 | 2/2008 | Popowski et al. |
| 2008/0097199 A1 | 4/2008 | Mullen |
| 2008/0228164 A1 | 9/2008 | Nicoson et al. |
| 2008/0243226 A1 | 10/2008 | Fernandez et al. |
| 2008/0281388 A1 | 11/2008 | Corbitt et al. |
| 2009/0024225 A1 | 1/2009 | Stubbs et al. |
| 2009/0030298 A1 | 1/2009 | Matthews et al. |
| 2009/0143747 A1 | 6/2009 | Dias et al. |
| 2009/0319046 A1 | 12/2009 | Krespi et al. |
| 2010/0010341 A1 | 1/2010 | Talpade et al. |
| 2010/0030072 A1 | 2/2010 | Casanova et al. |
| 2010/0042104 A1 | 2/2010 | Kota et al. |
| 2010/0234726 A1* | 9/2010 | Sirimanne ............ A61K 49/006 600/426 |
| 2011/0004094 A1 | 1/2011 | Subbs et al. |
| 2011/0028831 A1 | 2/2011 | Kent |
| 2011/0130655 A1 | 6/2011 | Nielson et al. |
| 2011/0313288 A1 | 12/2011 | Chi Sing et al. |
| 2012/0071845 A1* | 3/2012 | Hu .................... A61M 1/80 604/319 |
| 2013/0032962 A1 | 2/2013 | Liu et al. |
| 2013/0289390 A1 | 10/2013 | Herman et al. |
| 2013/0317275 A1 | 11/2013 | Stubbs |
| 2015/0112194 A1 | 4/2015 | Stubbs |
| 2016/0082286 A1 | 3/2016 | Stubbs et al. |
| 2016/0310286 A1* | 10/2016 | McJunkin ............ A61F 2/4611 |

* cited by examiner

EXPANDABLE TISSUE CAVITY MARKER DEVICES, SYSTEMS AND DEPLOYMENT METHODS

PRIORITY

This application claims the benefit of and priority to U.S. Provisional Application No. 62/624,977, filed Feb. 1, 2018, the entirety of which is incorporated herein by reference.

TECHNICAL FIELD

This disclosure relates generally to tissue markers and more particularly to expandable tissue cavity markers and corresponding systems and deployment methods.

BACKGROUND

Treatment of breast and other cancers often involves a biopsy, lumpectomy, or tumor or tissue resection. Many of these procedures now can be performed using minimally invasive procedures, such as by forming a small incision through which a biopsy tool or device can be inserted and removed. Minimally invasive procedures can be more comfortable and provide quicker healing for patients than open surgical procedures, while at the same time being less complex to perform.

After a biopsy, lumpectomy or resection procedure to remove tissue, localized radiation therapy can be provided to treat tissue remaining proximate the procedure area (e.g., at the "margin" of the cavity created when the tissue was removed) and reduce the chance of local recurrence in cases in which the removed tissue is found to be abnormal or cancerous and some abnormal or cancerous cells may have been left behind. To provide an accurate and lasting target for radiation, or simply to mark a tissue or cavity site for monitoring or future reference even if radiation therapy is not needed, radiopaque markers can be placed at the tissue removal site. While radiopaque markers can be placed at the site immediately after the tissue is removed, conventional markers typically are small in size and therefore can migrate within the cavity created when the tissue was removed or later as new tissue grows and fills the cavity. Conventional radiopaque markers also cannot fully define or mark the walls of the cavity.

To address this, some markers are mounted on or coupled to a support structure device that more completely fills the cavity volume. These support structure devices are large, however, and cannot be delivered via the same incision used in the minimally invasive procedure to remove the tissue. Moreover, these devices can be uncomfortable for patients both as they are delivered (and removed, if they must be later) and when they are in place.

SUMMARY

Embodiments of expandable tissue cavity markers and corresponding systems and deployment methods are disclosed.

In an embodiment, a tissue cavity marker for delivery to a tissue cavity via a delivery path between a minimally invasive surgical incision and the tissue cavity, the tissue cavity marker comprising an expandable pouch comprising at least one functional material and having a compressed state for delivery of the tissue cavity marker to the tissue cavity and an expanded state for residence within the tissue cavity, wherein injection of a fill material into the expandable pouch causes the expandable pouch to transition from the compressed state to the expanded state, wherein the expandable pouch is configured to retain the fill material therein in the expanded state, and wherein a diameter of the expandable pouch in the expanded state is at least about 1.5 times larger and not more than about 3.5 times larger than a diameter of the delivery path; and at least one radiopaque marker.

In an embodiment, a tissue cavity marking system for delivering a tissue cavity marker to a tissue cavity via a delivery path between a minimally invasive surgical incision and the tissue cavity, the system comprising a deployment device comprising a control mechanism at a proximal end and a tissue cavity marker aperture at a distal end, the control mechanism operable in use to deploy a tissue cavity marker from the tissue cavity marker aperture; and at least one tissue cavity marker comprising an expandable pouch comprising at least one functional material and having a compressed state for temporary arrangement in the tissue cavity marker aperture and an expanded state for residence within the tissue cavity, wherein injection of a fill material into the expandable pouch causes the expandable pouch to transition from the compressed state to the expanded state within the tissue cavity, wherein the expandable pouch is configured to retain the fill material therein in the expanded state, and wherein a diameter of the expandable pouch in the expanded state is at least about 1.5 times larger and not more than about 3.5 times larger than a diameter of the distal end of the deployment device; and at least one radiopaque marker.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1A:
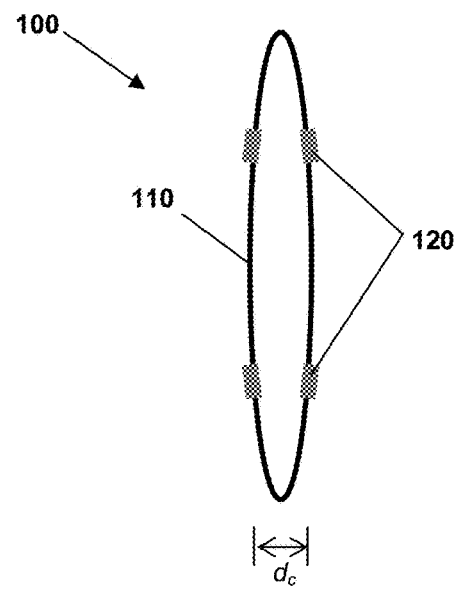
FIG. 1A depicts an expandable tissue cavity marker in a compressed state according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Embodiments relate to expandable tissue cavity markers and corresponding systems and deployment methods. In one embodiment, an expandable tissue cavity marker comprises a pouch and at least one radiopaque marker element coupled with the pouch. The pouch can transition between a compressed state, in which a profile or dimension of the tissue cavity marker is reduced such that the tissue cavity marker can be deployed through a minimally invasive surgical procedure incision, and an expanded state, in which a profile or dimension of the tissue cavity marker is increased such that the tissue cavity marker fills or defines a volume of a tissue cavity. In one embodiment, the pouch can be transformed between the compressed state and the expanded state by delivery of a fill material into the pouch. The pouch can comprise one or more functional materials in embodiments, including materials that provide an anti-infection, hemostasis, anti-migration, medicinal, or other function to the tissue cavity marker.

In another embodiment, an expandable tissue cavity marker comprises a pouch, a scaffold structure arranged in or on the pouch, and at least one radiopaque marker element coupled with either the pouch or the scaffold structure. Both the pouch and the scaffold structure can transform between a compressed state, in which a profile or dimension of the tissue cavity marker is reduced such that the tissue cavity marker can be deployed through a minimally invasive surgical procedure incision, and an expanded state, in which a profile or dimension of the tissue cavity marker is increased such that the tissue cavity marker fills or defines a volume of a tissue cavity. In one embodiment, the pouch and the scaffold structure can be transformed between the compressed state and the expanded state by delivery of a fill material into the pouch. One or both of the pouch or the scaffold structure can comprise one or more functional materials in embodiments, including materials that provide an anti-infection, hemostasis, anti-migration, medicinal, or other function to the tissue cavity marker.

Embodiments also relate to expandable tissue cavity marker deployment devices and systems. In one embodiment, a deployment device comprises a catheter, syringe or other tool having a proximal (operator) end and a distal (patient) end. The proximal end comprises a control mechanism by which the deployment device can be operated during use. The distal end comprises an aperture into which an expandable tissue cavity marker in the compressed state can be loaded. The tissue cavity marker can comprise a pouch with or without a scaffold structure. The distal end can be inserted through a minimally invasive surgical incision to deliver the tissue cavity marker to a target site, such as a tissue cavity. At the target site, the control mechanism can be used to deploy and release the tissue cavity marker from the deployment device. As it is being deployed, or after it has been deployed, the tissue cavity marker can be transitioned to the expanded state, such as by using the deployment device to deliver a fill material to the pouch. In other embodiments, the fill material can be delivered to the pouch using a separate device or tool.

Figure 2A:
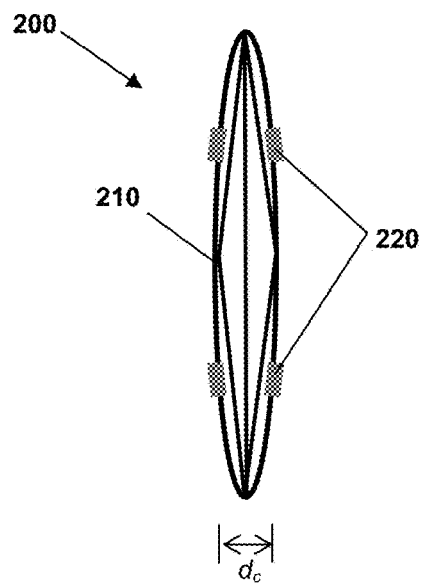
FIG. 2A depicts an expandable tissue cavity marker with a scaffold structure, in a compressed state according to an embodiment.

Throughout this disclosure, some like elements are referenced similarly in different figures, iterated by factors of 100 (e.g., 100 in FIG. 1A and 200 in FIG. 2A each refer to tissue cavity markers but different embodiments thereof). Additionally, the drawings are not necessarily to scale, and the relative shapes and sizes of various components in some embodiments may not be exactly as depicted.

Figure 1B:
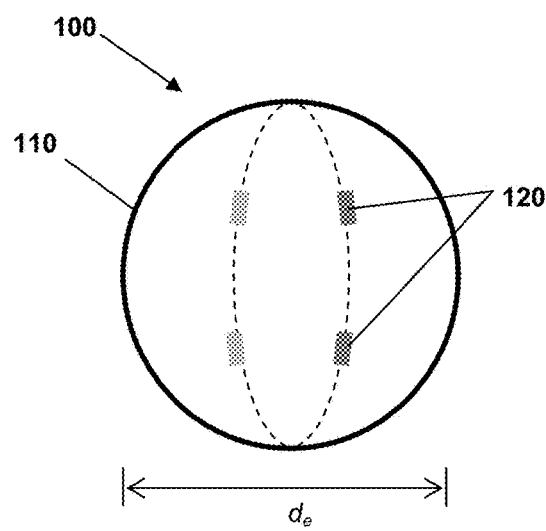
FIG. 1B depicts the expandable tissue cavity marker of FIG. 1A in an expanded state.
Figure 1C:
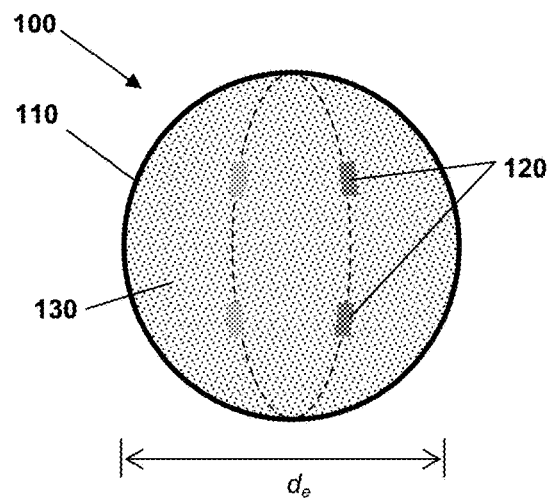
FIG. 1C depicts the expandable tissue cavity marker of FIG. 1B with a fill material.

Referring to FIGS. 1A, 1B and 1C, one embodiment of an expandable tissue cavity marker 100 is depicted. Tissue cavity marker 100 comprises an expandable pouch 110 and at least one radiopaque marker 120 coupled with pouch 110. In FIG. 1A, tissue cavity marker 100 and pouch 110 are depicted in a compressed or non-expanded state. In FIG. 1B, tissue cavity marker 100 and pouch 110 are depicted in an expanded state, and in FIG. 1C tissue cavity marker 100 is depicted in the expanded state and comprising a fill material 130 within pouch 110.

In this disclosure, the expanded state of tissue cavity marker 100 (and pouch 110) is the state or configuration of tissue cavity marker 100 when it is deployed and resident in a tissue cavity, while the compressed state of tissue cavity marker 100 (and pouch 110) is a state that enables at least one dimension (e.g., a diameter, radius, width or volume) but sometimes two or all three dimensions of tissue cavity marker 100 to be temporarily reduced in order to enable or ease delivery and deployment of tissue cavity marker 100 in a tissue cavity via a minimally invasive surgical incision. For example, in one embodiment at least two dimensions of tissue cavity marker 100 in its expanded state are greater than a length of a minimally invasive surgical incision, but in its compressed state these dimensions are reduced such that tissue cavity marker 100 can be delivered via the minimally invasive surgical incision. Minimally invasive surgical incisions can be about 3 centimeters (cm) long or less, such as about 2 cm long or less, or about 1 cm long or less, or less than about 7 mm long, for example about 6 mm long in one example. A range of minimally invasive surgical incision lengths is between 5 mm and 1 cm in one example. In some embodiments, tissue cavity marker 100 can have a third, rest state, which is a state in which tissue cavity marker 100 is not actively compressed, e.g., for deployment, but also is not expanded.

Pouch 110 of tissue cavity marker 100 is generally of a size and three-dimensional shape with both sufficient flexibility (to be compressed for delivery and deployment, and then expanded once in place) and rigidity (to maintain, for some amount of time and aided by fill material 130 or other structures in some embodiments, an expanded state) to be used as a marker in a tissue cavity created by a biopsy, lumpectomy or other resection of tissue. In embodiments, pouch 110 is compatible with a minimally-invasive deployment device. For example, pouch 110 or tissue cavity marker 100 overall can have a diameter $d_c$ in its compressed state (see FIG. 1A) of about 10 millimeters (mm) or less, such as about 8 mm or less, about 7.5 mm or less, about 7 mm or less, about 6.5 mm or less, about 6 mm or less, or about 5 mm or less, in various embodiments. After deployment and in its expanded state, pouch 110 or tissue cavity marker 100 overall can have a diameter of about 10 mm or more, such as about 12 mm or more, about 15 mm or more, about 20 mm or more, about 25 mm or more, or about 30 mm or more, in various embodiments. A range of diameters $d_e$ (see FIGS. 1B and 1C) of pouch 110 or tissue cavity marker 100 overall in the expanded state is about 10 mm to about 30 mm in one example.

In one particular example, a diameter $d_c$ of pouch 110 in its compressed state is less than about 7.5 mm such that it can be delivered by a device having a diameter of about 7.5 mm, and a diameter $d_e$ of pouch 110 is about 20 mm. In this example, a diameter of the delivery path taken by the distal end of a deployment device between the incision and the tissue cavity is also about 7.5 mm or slightly larger, such as about 7.6 mm or 7.7 mm, though the path may partially collapse after the distal end of the deployment device is withdrawn and removed. In various embodiments, a diameter of the distal end of the deployment device is between about 6 mm and about 8 mm, such as between about 6.4 mm and about 7.6 mm, or about 6.5 mm in embodiment, or about 7.5 mm in another embodiment. The difference between diameter $d_e$ of pouch 110 and the 7.5 mm diameter of the insertion portion of the deployment device (and therefore also the approximate diameter of the delivery path) can discourage or prevent migration of tissue cavity marker 100 along the track of the deployment device.

In various embodiments, the diameter $d_e$ of pouch 110 is at least about 1.5 times, at least about 2 times, at least about 2.5 times, at least about 3 times, at least about or at least about 5 times the diameter of the insertion portion or distal end of the deployment device. Thus, the diameter $d_e$ of pouch 110 can be about 1.5 times to about 5 times, or about 1.6 times to about 3 times, the diameter of the insertion portion or distal end of the deployment device. At the same time, the diameter $d_e$ of pouch 110 is not more than about 10 times, or not more than about 8 times, or not more than about 7 times, or not more than about 6 times, or not more than about 5 times the diameter of the insertion portion of the deployment device. For example, in one embodiment the diameter $d_e$ of pouch 110 is at least about 3 times but not more than about 5 times the diameter of the insertion portion of the deployment device.

In some embodiments, diameter $d_e$ in an expanded but unfilled state (FIG. 1B) and diameter $d_e$ in a filled state (FIG. 1C) may not be identical. For example, fill material 130 can cause the diameter to increase slightly if a sufficient amount of fill material 130 is added to pouch 110 and pouch 110 has at least some elasticity. In some situations, it can be advantageous to completely fill or slightly overfill pouch 110 with fill material 130 as the pressure provided by pouch 110 on the tissue margin around the tissue cavity can ease or prevent bleeding. This also can be achieved by selecting a size of pouch 110 with a diameter $d_e$ that is the same as or slightly larger than the diameter of the tissue cavity. In another example, underfilling of pouch 110 with fill material 130 can result in the diameter decreasing slightly if pouch 110 is not rigid.

Pouch 110 generally comprises a pouch, pocket, sac, membrane, bag or other structure with an exterior perimeter that defines an internal volume in which fill material 130 can be retained. Pouch 110 can comprise an uninterrupted, unitary body in some embodiments, while in other embodiments pouch can comprise one or more seams, fill apertures, or other features. Pouch 110 can comprise a cloth or other woven material, a mesh material, a non-woven material, a fiber material, or another material or combination of these or other materials. The material can be stiffened, coated, permeated, or otherwise treated by another material or process in various embodiments. In various embodiments, pouch 110 can be porous or non-porous.

In some embodiments, pouch 110 comprises a functional or multifunctional material. For example, pouch 110 can comprise a material with one or more of anti-infection, anti-migration or hemostasis properties. Materials with anti-infection properties are those capable of acting against infection, such as by preventing the occurrence of an infectious agent, inhibiting the spread of an infectious agent, or harming or killing the infectious agent. One example of a material with anti-infection properties is TYRX available from MEDTRONIC. Materials with anti-migration properties are those that inhibit movement such that the structure remains in an intended location or orientation. One example of a material with anti-migration properties is PROGRIP available from MEDTRONIC. Materials with hemostasis properties are those that inhibit the flow of blood. One example of a material with hemostasis properties is VERISET available from MEDTRONIC. In some embodiments, pouch 110 also comprises a material that bioabsorbable or resorbable.

Pouch 110 can comprise these or other functional or multi-functional materials with the aforementioned or other properties in various embodiments 110. For example, in some embodiments pouch can comprise a medicament or drug to treat a tissue surrounding the cavity in which tissue cavity marker 100 is deployed. Pouch 110 itself can comprise a functional or multifunctional material in its entirety, or select portions of pouch 110 can comprise a functional or multifunctional material, or a functional or multifunctional material can be applied to at least a portion of pouch 110, or some other arrangement or technique for incorporation a functional or multifunctional material into or on pouch 110 can be used.

In some embodiments, pouch 110 or a portion or feature thereof (e.g., scaffold structure 240 discussed in more detail below) comprises a shape-memory alloy material, such as Nitinol. Shape-memory alloys are not bioabsorbable but may have application in some procedures or situations in which bioabsorbability is not desired or required.

In some embodiments, pouch 110 can comprise features or structures in addition to, or in or on, the pouch itself. For example, pouch 110 can comprise a fill aperture (not shown), such as a one-way valve, by which fill material 130 can be added to pouch 110. In one embodiment, the fill aperture also comprises a deployment aperture via which tissue cavity marker 100 is removably coupled with a device to facilitate delivery and deployment to a tissue cavity. In another embodiment, pouch 110 can comprise a self-healing material or portion such that pouch 110 can be pierced by a device delivering fill material 130 and after removal of the device the piercing closes and fill material 130 is retained within pouch 110. In yet another embodiment, a clip, suture, or other closure device can be used to close a fill aperture or otherwise seal pouch 100 after fill material 130 is injected therein. In still other embodiments, pouch 110 can comprise a porous material, with fill material 130 selected such that its properties prevent it from leaking or otherwise escaping the confines of pouch 110. Materials and features of various embodiments of pouch 110 and fill material 130 are discussed below.

Pouch 110 of tissue cavity marker 100 can comprise a variety of different three-dimensional shapes in an expanded state in various embodiments, such as the generally spherical configuration shown in FIGS. 1B and 1C. In other embodiments, pouch 110 can be ovular, ovoid, spheroid, ellipsoid, cylindrical, cuboid, conical, prismatic, pyramid, or some other three-dimensional shape, including a combination of two or more of these shapes. A particular tissue cavity size, configuration, patient anatomy or type (e.g., human adult, human pediatric, veterinary), deployment device or situation, or other characteristic may benefit from a custom shape, which can be created in some embodiments. For example, tissue cavity marker 100 is sized and shaped for residence in a tissue cavity and can be sized and shaped so as to just fit within a particular cavity or to be slightly compressed when installed in and restrained by the tissue surrounding the cavity. In at least this sense, tissue cavity marker 100 can physically interact with at least a portion of a margin of the cavity in which it is deployed.

Tissue cavity marker 100 also comprises at least one radiopaque marker 120 in embodiments. Radiopaque materials are those that are opaque to and therefore visible on X-ray or other radiation images. Examples of radiopaque materials include metals (e.g., titanium, nonferromagnetic stainless steel) as well as some plastics and polymers known to those of ordinary skill in the art. Including radiopaque markers 120 on tissue cavity marker 100 makes it possible to locate markers 120 (and thereby the cavity in which tissue cavity marker 100 is resident) on radiation images after tissue cavity marker 100 is deployed in the cavity, including after pouch 110 is resorbed in embodiments in which pouch 110 is bioabsorbable. The longevity of radiopaque markers 120 can be helpful for follow-up treatments (e.g., targeted radiation therapy) and ongoing monitoring of the cavity and tissue margins of the cavity, while coupling radiopaque markers 120 with pouch 110 can prevent migration until new tissue has grown into a tissue cavity.

The number, size and relative arrangement of markers 120 can vary from those depicted in FIGS. 1A, 1B and 1C. As depicted, tissue cavity marker 100 comprises four markers 120 arranged in or on a surface of pouch 110. In other embodiments, more or fewer markers 120 can be used, and the placements and relative arrangement of markers 120 can vary. Additionally, some markers 120 may be smaller, larger, or differently shaped than other markers 120. The compressed and expanded states of tissue cavity marker 100 can be considered when arranging a plurality of markers 120 thereon. For example, two markers 120 can be staggered such that when tissue cavity marker 100 is in the compressed state of FIG. 1A adjacent markers 120 do not align in ways that interfere with one another, and a profile of tissue cavity marker 100 can still be sufficiently reduced to be loaded into a deployment device and delivered by a minimally invasive surgical incision.

Structurally, markers 120 can comprise clips that are coupled to pouch 110 in one embodiment. This coupling can be accomplished in a variety of ways, such as by folding, wrapping, crimping, embedding, adhering, applying, or otherwise attaching a portion of marker material to a portion of pouch 110. In other embodiments, markers 120 can be coupled with pouch 110 by being at least partially embedded or arranged therein (e.g., within pouch 110). In still other embodiments, pouch 110 can be formed in or on one or more markers 120, such as by being woven into or injection-molded through a marker 120 that comprises a ring, tube or other structure that is hollow or comprises an aperture through which a portion of pouch 110 can pass. In further embodiments, one or both of pouch 110 and markers 120 can be three-dimensionally printed, together or separately.

In embodiments, tissue cavity marker 100 transitions from a compressed (or rest) state to an expanded state by insertion of a fill material 130. In other words, delivery of fill material 130 into pouch 110 causes pouch 110 to expand. In one embodiment, a volume of fill material 130 is provided to completely fill pouch 110, causing tissue cavity marker 100 to fully occupy the cavity. In other embodiments, the volume of fill material 130 to use in any particular situation can be selected by a medical professional, including by adjustment during filling (e.g., continuing to inject fill material 130 until a desired state is reached, or having the ability to remove injected fill material 130). Fill material 130 can be delivered into pouch 110 in a variety of ways, such as by injection by the same deployment device that delivers and deploys tissue cavity marker 100 or by a separate device, for example a syringe.

Fill material 130 can comprise a gas, liquid, gel, powder, particulate, or other material or combination of materials (e.g., a particulate suspended in a liquid). Example materials include air, water, saline, a bioabsorbable material (e.g., DURASEAL, a bioabsorbable hydrogel available from MEDTRONIC), a biocompatible hydrogel, collagen (e.g., PERMACOL, a collagen paste available from MEDTRONIC), or a combination of these or other suitable materials. In one embodiment, fill material 130, like pouch 110 discussed above, can comprise a functional or multi-functional material, such as one that provides anti-infection or hemostasis functions. In still other embodiments, fill material 130 can comprise a material that changes state, such as from a liquid when injected to a gel after some amount of time passes, or from a dehydrated gel to a hydrated gel upon injection of saline. The state transition can be effected by combination or compounding with another material, a temperature change, passage of time, being acted on by an external factor (e.g., application of radiation), or some other factor.

Figure 2B:
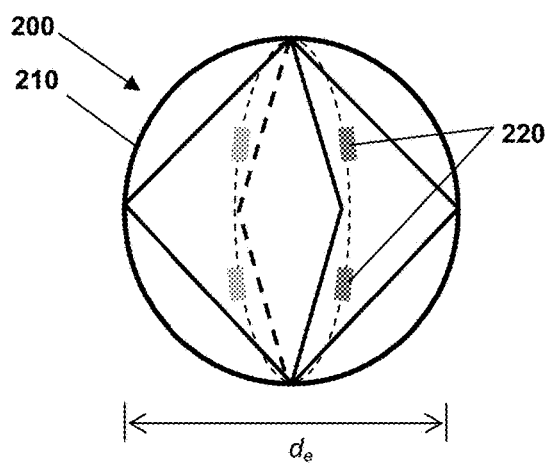
FIG. 2B depicts the expandable tissue cavity marker of FIG. 2A in an expanded state.
Figure 2C:
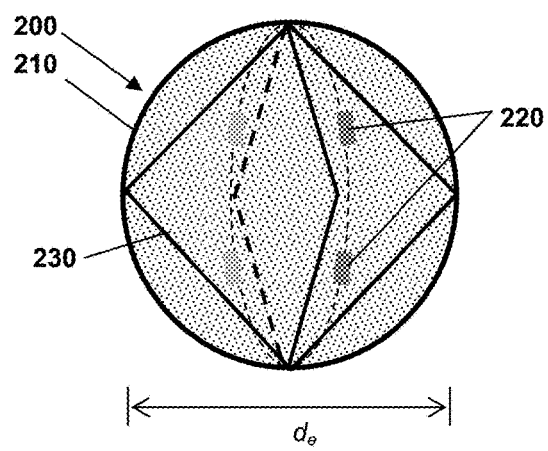
FIG. 2C depicts the expandable tissue cavity marker of FIG. 2B with a fill material.

Referring to FIGS. 2A, 2B and 2C, a tissue cavity marker 200 comprises a pouch 210, at least one marker 220, and a scaffold structure 240. The materials, properties, behaviors, and other characteristics of tissue cavity marker 200, pouch 210 and markers 220 are similar to or the same as those discussed above with respect to tissue cavity marker 100, pouch 110 and markers 120, respectively, unless otherwise discussed explicitly herein.

Scaffold structure 240 can provide additional structural support to tissue cavity marker 100, particularly in an expanded state. As depicted in the embodiment of FIG. 2A, scaffold structure 240 can be present within pouch 210 in a compressed state. In other words, scaffold structure 240 can be arranged within pouch 210 prior to tissue cavity marker 100 being delivered to and deployed with a tissue cavity. In another embodiment, tissue cavity marker 100 can be delivered without scaffold structure 240, then scaffold structure 240 can be provided later, such as before, with or after fill material 230. In yet another embodiment, scaffold structure 240 can be delivered and deployed to a tissue cavity first, and then pouch 210 can be delivered and deployed into or around scaffold structure 240, followed by fill material 230. In a further embodiment, pouch 210 and scaffold structure 240 are integrally formed with one another. In any embodiment, scaffold structure 240, like pouch 210, also has compressed and expanded states to facilitate delivery and deployment via a minimally invasive surgical incision as discussed herein.

Scaffold structure 240 can comprise a stent-type structure, a spring or coil structure, a helical structure, a shape-memory material structure, a sponge-type material structure, a dehydrated gel material structure, or some other material or structure. For example, scaffold structure 240 can comprise one of the shape-memory or other materials discussed herein with respect pouch 110. In embodiment in which scaffold structure 240 comprises a stent or spring structure, the stent or spring structure can comprise compression spring-type structures that are compressed in the compressed state of pouch 210 and become uncompressed in the expanded state of pouch 210 such that they provide internal structural support to pouch 210 in the expanded state. In still other embodiments, and departing from the embodiment depicted in FIGS. 2A, 2B and 2C, scaffold structure 240 can be integrated with or comprise the same material as that of radiopaque markers 120 or 220.

In FIGS. 2A, 2B and 2C, scaffold structure 240 comprises a plurality of angular members, which can be coupled with another at hinge or flex points. This is but one example embodiment of scaffold structure 240. In other embodiments, scaffold structure 240 can comprise more or fewer members, curved rather than or in addition to angular members, a spring or helical structure, or some other configuration that can be compressed for deployment and delivery and expand with a tissue cavity to provide support to pouch 210. For example, in one embodiment scaffold structure 240 can comprise a unitary element, such as a helical body or spring. In yet another embodiment, scaffold structure 240 can be integrated with or comprise part of fill material 230.

Figure 3A:
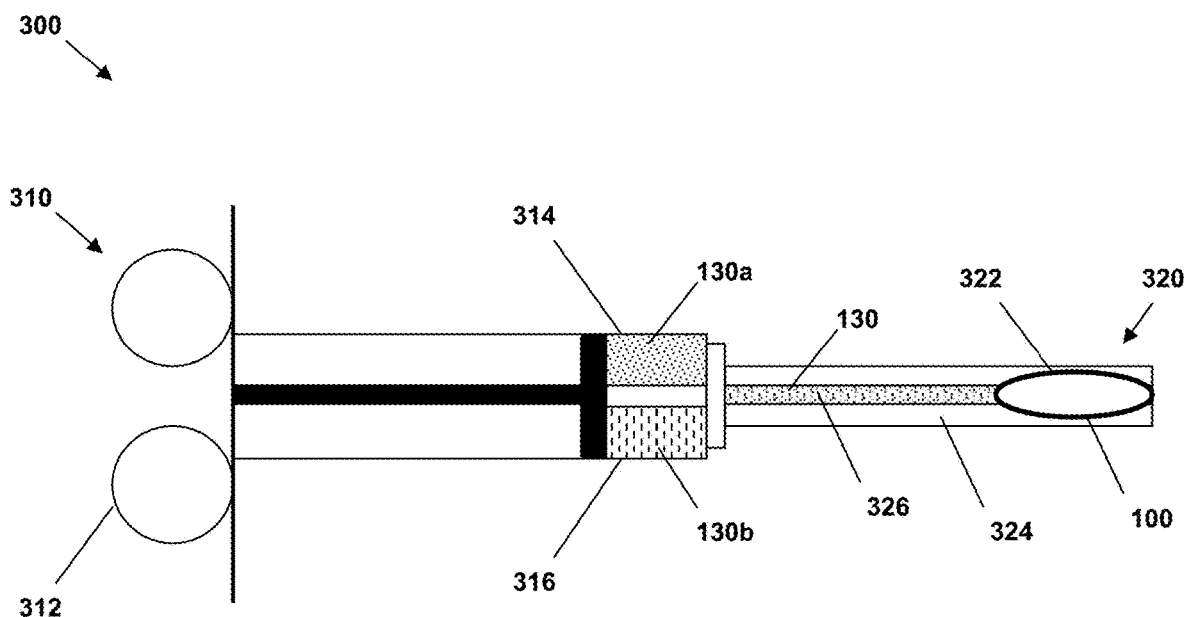
FIG. 3A depicts a deployment device loaded with an expandable tissue cavity marker according to an embodiment.
Figure 3B:
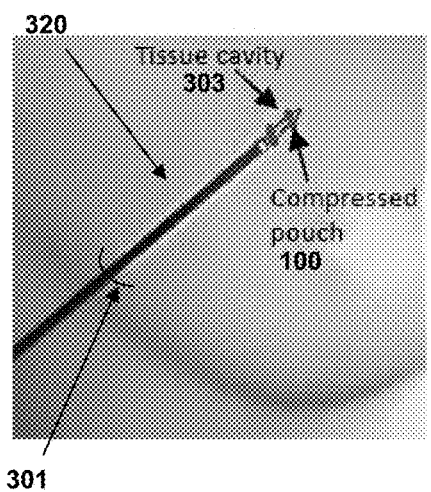
FIG. 3B depicts a distal portion of a deployment device delivering an expandable tissue cavity marker to a tissue cavity according to an embodiment.
Figure 3C:
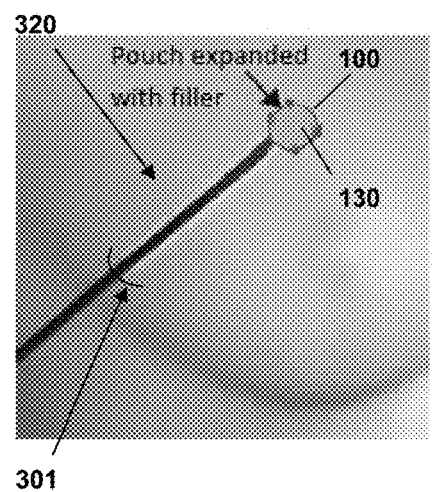
FIG. 3C depicts a distal portion of a deployment device delivering a fill material to the expandable tissue cavity marker of FIG. 3B.

Referring to FIGS. 3A, 3B and 3C, and returning to the example embodiment of tissue cavity marker 100 of FIGS. 1A, 1B and 1C, a deployment device 300 is depicted. Deployment device 300 comprises a proximal control end 310 and a distal delivery end 320. Here and throughout, "proximal" is used with respect to an operator/physician end (310) of deployment device 300, and "distal" is used with respect to a patient or delivery end (320) of deployment device 300.

Deployment device 300 can comprise a catheter, syringe or other device into which a tissue cavity marker (e.g., tissue cavity marker 100) can be loaded in its compressed state, delivered to a cavity site via a minimally invasive surgical incision, deployed within the cavity, and transitioned from the compressed state to the expanded state, such as by injection of filler material 130. In some embodiments, the transition from compressed to expanded state of tissue cavity marker 100 can be accomplished using at least one additional tool or device.

Proximal control end 310 of deployment device 300 comprises a control system 312 (depicted in simplified form but appreciate by those of skill in the art) via which deployment device 300 can be controlled. In particular, control system 312 allows an operator of deployment device 300 to manipulate deployment device 300 to insert distal delivery end 320 through an incision, guide distal delivery end 320 to a delivery site (such as a tissue cavity), and control deployment of tissue cavity marker 100 from distal delivery end 320 to the delivery site. Additionally, in the embodiment of FIG. 3A, control system 312 further enables an operator to facilitate delivery of one or more fill materials 130 (discussed in more detail below). Control system 312 can comprise one or more of a plunger (depicted in FIG. 3A), guidewire, mechanical actuator, robotic or computer-assisted control mechanism, or some other control mechanism that can be manipulated in order to control deployment device 300 and effect delivery and deployment of tissue cavity marker 100 and injection of one or more fill materials 130.

In FIG. 3A, deployment device 300 and control system 312 are configured to deliver fill material 130 that comprises a two-part compound 130a and 130b that is mixed to form fill material 130. Compound 130a is arranged in chamber 314, and compound 130b is arranged in chamber 316. In other embodiments, deployment device 300 and control system 312 can accommodate other multi-part compounds (e.g., three-part compound) or be configured for a single-part fill material 130. In yet another embodiment, deployment device 300 and control system 312 can be configured to deliver multi-part fill materials in which the multiple parts are delivered sequentially rather than mixed as in FIG. 3A.

In still other embodiments, as discussed above, fill material 130 can be delivered using a separate deployment device.

Distal delivery end 320 comprises a distal end aperture 322 into which compressed tissue cavity marker 100 can be loaded. In some embodiments, distal end aperture 322 can comprise or be part of a cannula, trocar, catheter or other hollow device forming part or all of distal delivery end 320 or deployment device 300. Though many different configurations and types of devices can be used in various embodiments, they will be generally referred to herein, inclusively, as deployment device 300 and distal delivery end 320. Distal delivery end 320 can be rigid or flexible, and straight, curved or angled, in various embodiments. In some particular embodiments, a first portion of distal delivery end 320 can be rigid, and a second portion of distal delivery end 320 can be flexible. Similarly, a first portion of distal delivery end 320 can be straight, and a second portion of distal delivery end 320 can be curved. At least a portion of distal delivery end 320 being rigid can be advantageous in some embodiments to assist an operator in manipulating deployment device 300 to maneuver tissue cavity marker 100 into place in a tissue cavity, though some operators may prefer a degree of flexibility.

In the embodiment of FIG. 3A, distal delivery end 320 comprises at least two lumens: an outer lumen 324 comprising distal end aperture 322 and an inner lumen 326 for delivery of fill material 130. In such an embodiment, control system 312 can facilitate independent operation of outer lumen 324 and inner lumen 322, as discussed in more detail below. In another embodiment, inner lumen 326 can comprise an array of lumens for delivering multiple compounds or components. In FIG. 3A, outer lumen 324 has a larger diameter than inner lumen 326, and inner lumen 326 is arranged within outer lumen 324 such that the two lumens are coaxial. In other embodiments, outer lumen 324 and inner lumen 326 can instead be adjacent one another or have some other relative arrangement.

In FIG. 3A, tissue cavity marker 100 (in its compressed state) is loaded into distal end aperture 322, and fill material compounds 130a and 130b are loaded into chambers 314 and 316, respectively. One tissue cavity marker 100 can be loaded into distal end aperture 322, or multiple tissue cavity markers 100 can be loaded into distal end aperture 322 for sequential delivery, such as in a case in which multiple tissue cavities of a single patient are to be marked. In some embodiments, tissue cavity marker 100 can be preloaded into distal end aperture 322, and compounds 130a and 130b can be preloaded into chambers 314 and 316, respectively. In such an embodiment, deployment device 300 can be provided in sterile packaging and need only be removed from the packaging by a physician or other medical professional in order to deliver and deploy tissue cavity marker 100. In other embodiments, tissue cavity marker 100 can be provided in separate sterile packaging or in some other configuration separate from but relative to deployment device 300. For example, tissue cavity marker 100 can be provided preloaded in its compressed state in distal delivery end 320, with distal delivery end 320 provided in sterile packaging separate from proximal control portion 310 of deployment device 300, which may be sterilizable and reusable in some embodiments. Prior to use, distal delivery end 320 can be removed from its packaging, coupled with proximal control portion 310, and used to deliver and deploy tissue cavity marker 100 at a desired site. Similarly, compounds 130a and 130b can be provided separately from deployment device 300, with a desired amount of selected compounds 130a and 130b obtained and loaded into chambers 130a and 130b prior to use.

Still other ways of providing tissue cavity marker 100, fill material 130, deployment device 300 or portions thereof can be implemented in other embodiments. For example, it may be helpful to provide, separate from deployment device 300, a variety of tissue cavity markers (100, 200, etc.) and fill materials 130 from which a physician or other medical professional can select an appropriate one for any particular cavity, patient or procedure. In general, however, it can be convenient for tissue cavity marker 100 (in its compressed state) and fill material 130 to be preloaded in deployment device 300 to avoid a physician having to transition tissue cavity marker 100 from its rest state to its compressed state in order to load tissue cavity marker 100 into deployment device 300. Nevertheless, there may be situations in which this is necessary or desired (e.g., according to physician preference).

Referring to FIG. 3B, deployment device 300 is depicted in use, with distal delivery end 320 inserted via a minimally invasive incision 301 in a patient's skin to an internal tissue cavity 303, such as one created by a breast tissue biopsy or lumpectomy. In some embodiments, tissue cavity marker 100 in its compressed state is deployed in cavity 303 from distal delivery end 320. For example, the tip of distal delivery end 320 and outer lumen 324 can be advanced to a proximal edge of cavity 303, and tissue cavity marker 100 can be deployed from distal end aperture 322 by continuing to advance inner lumen 326 within outer lumen 324 using control system 312 as outer lumen 324 is maintained at the proximal edge of cavity 303 to deliver tissue cavity marker 100 into cavity 303. In another embodiment, inner lumen 326 begins partially within tissue cavity marker 100, the tip of distal delivery end 320 and outer lumen 324 can be advanced to a distal edge of cavity 303, and tissue cavity marker 100 can be deployed from distal end aperture 322 by maintaining positioning of inner lumen 326 proximate the distal edge of cavity 303 while retracting outer lumen 324 using control system 312, thereby delivering tissue cavity marker 100 into cavity 303. In such an embodiment, fill material 130 can be injected into tissue cavity marker 100 during delivery and deployment, or afterward.

In some embodiments, image-guided surgical techniques can be used to view distal delivery end 320 as it is directed to cavity 303 and ensure tissue cavity marker 100 is placed within cavity 303 prior to or after deployment of tissue cavity marker 100 from deployment device 300. In these embodiments, deployment device 300 can comprise a colorant, radiopaque or radiographic marker or filler, or other additive in or coating on distal delivery end 320 to aid in visualization or navigation.

Referring to FIG. 3C, tissue cavity marker 100 is transitioned to its expanded state within cavity 303. In the embodiment of FIG. 3C, this is accomplished by injecting fill material 130 into cavity tissue cavity marker 100 via inner lumen 326 (see FIG. 3A) in distal delivery end 320. As previously mentioned, this can be done using deployment device 300 (as tissue cavity marker 100 is being deployed within cavity 303, or after tissue cavity marker 100 is deployed within cavity 303) or by using a separate device (e.g., a syringe or separate fill material delivery device) after tissue cavity marker 100 is deployed within cavity 303 and deployment device 300 is retracted and removed.

In embodiments using tissue cavity marker 200 comprising scaffold structure 240, the delivery and filling/expansion processes can be modified. For example, in one embodiment in which scaffold structure 240 is arranged in or otherwise coupled with pouch 210, injecting fill material 230 into pouch 210 can cause scaffold structure 240 to expand along with pouch 210. In another embodiment, scaffold structure 240 can be inserted into pouch 210 before or with fill material 230, such as by deployment device 300. In such an embodiment, deployment device 300 can comprise one or more additional inner lumens (not depicted) to deliver and deploy scaffold structure 240, or scaffold structure 240 can be delivered via inner lumen 326 with fill material 230, or scaffold structure 240 can be arranged sequentially after pouch 210 in distal end aperture 322 for delivery into pouch 210 after pouch 210 is already delivered to cavity 303. In some embodiments, one or both of pouch 110, 210 or scaffold structure 240 can be removably or temporarily coupled with inner lumen 326 to aid delivery and deployment to tissue cavity 303. In any embodiment, either or both of fill material 130, 230 or scaffold structure 240 can be delivered by deployment device 300 or some other, separate device.

Upon transition to its expanded state, tissue cavity marker 100 will remain in cavity 303, and distal delivery end 320 can be retracted and removed. Because tissue cavity marker 100 generally will be left in cavity 303 indefinitely, incision 301 can be closed. As previously mentioned, tissue cavity marker 100, and thereby cavity 303, can be located on X-ray or other images via radiopaque markers 120, 220 (see FIGS. 1A, 1B, 1C, 2A, 2B and 2C) and will not migrate from cavity 303 because tissue cavity marker 100 holds them in place. Over time, new tissue will grow into cavity 303 and around tissue cavity marker 100, and tissue cavity marker 100 (including both pouch 110, 210 and scaffold structure 240) will resorb, leaving only radiopaque markers 120, 220 behind in the tissue now filling former cavity 303.

While the examples discussed herein include tissue cavity marker 100 loaded in its compressed state into distal end aperture 322 of distal delivery end 320 of deployment device 300, in other embodiments tissue cavity marker 100 can be loaded into distal end aperture 322 in its rest state or a partially expanded state.

Figure 4:
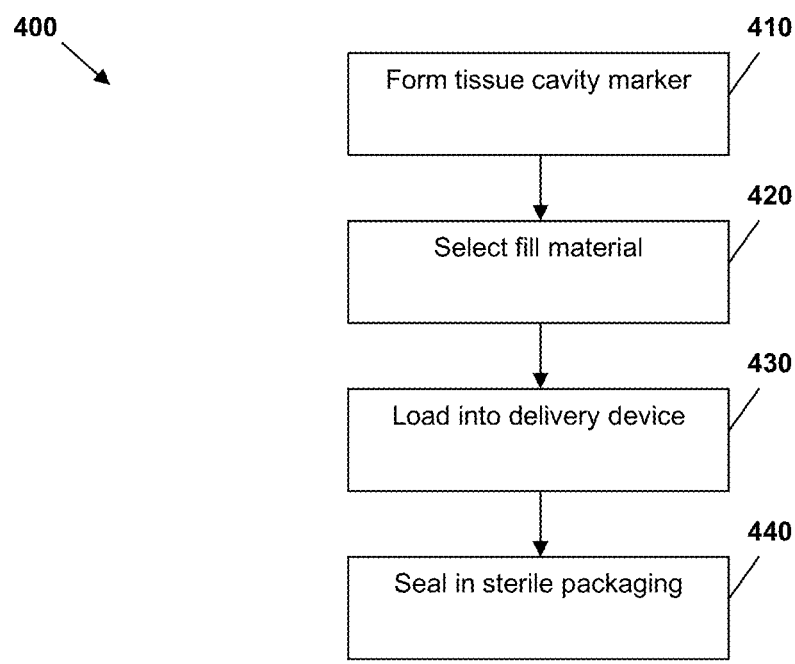
FIG. 4 is a flowchart of a method of forming an expandable tissue cavity marker according to an embodiment.

Referring to FIG. 4, a method 400 of providing a tissue cavity marker, such as tissue cavity marker 100 or tissue cavity marker 200, is depicted. At 410, a tissue cavity marker is formed, such as comprising a pouch and optionally a scaffold structure. Forming the tissue cavity marker can include selecting an expanded shape of the tissue cavity marker, and cutting, molding, extruding, three-dimensionally printing, or otherwise manipulating a material to enable the desired complex, three-dimensional expanded shape. Forming the tissue cavity marker also can include one or more of forming at least one radiopaque marker, coupling at least one radiopaque maker to the pouch or the scaffold structure, forming the scaffold structure, or inserting the scaffold structure into the pouch or otherwise coupling the scaffold structure with the pouch, among other tasks. At 420, a fill material can be selected. Selecting a fill material can include one or more of forming a fill material or assembling a plurality of compounds to be mixed to form the fill material. At 430, one or both of the tissue cavity marker and the fill material can be loaded into a deployment device. This can include loading multiple compounds of the fill material into distinct chambers of the deployment device. The tissue cavity marker can be loaded into the deployment device in a rest state, a compressed state, or some other suitable state. At 440, the loaded deployment device or an individual tissue cavity marker can be sealed in sterile packaging. In various embodiments, the order of activities depicted in FIG. 4 can be changed, additional activities can be inserted, and depicted activities can be omitted.

Embodiments of the tissue cavity markers discussed herein provide advantages with respect to conventional tissue markers. For example, the ability of tissue cavity marker to be transitioned from a compressed or rest state to an expanded state enables the tissue cavity marker to be delivered via an incision with a length or other dimension that is smaller than a diameter or other dimension of the tissue cavity marker in its expanded state. The shape, dimensions and other characteristics of the tissue cavity maker in various embodiments also can be selected to provide a snug or custom fit of the tissue cavity marker within a cavity, thereby providing a secure support structure for the radiopaque marker(s) coupled to the tissue cavity marker and inhibiting the radiopaque markers from migrating within the cavity. Moreover, embodiments comprising a scaffold structure can provide additional support within the cavity and for radiopaque markers. The configuration of the tissue cavity marker and its ability to expand three-dimensionally within the cavity also provides for a plurality of radiopaque markers to be used to more completely define the margins of the cavity. Once new tissue has grown into the cavity and around the radiopque markers, the markers are less likely to migrate, such that the tissue cavity marker can be formed from a bioabsorbable material and need not be removed by another surgical procedure. This can increase patient comfort and recovery, reduce expense, and eliminate procedures (as well as the likelihood for complications) by eliminating the need for a second procedure to remove the tissue cavity marker. Additionally, the ability to customize the shape of the tissue cavity marker, whether or not a scaffold structure is used, and the type of fill material means it can be used in a variety of different places and procedures, including but not limited to breast tissue biopsies and lumpectomies as well as other tissue biopsy sites. Also, tissue cavity makers comprising functional materials (e.g., for any or all of the pouch, scaffold structure, or fill material) can provide additional benefits related to anti-infection, hemostasis or anti-migration of the tissue cavity marker or its components within a tissue cavity.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A tissue cavity marker for delivery to a tissue cavity via a delivery path between a minimally invasive surgical incision and the tissue cavity, the tissue cavity marker comprising:
   an expandable pouch comprising:
      at least one functional material;
      an exterior perimeter that defines an internal volume;
      a fill aperture on the exterior perimeter; and
      at least one radiopaque marker,
      the expandable pouch having a compressed state for delivery of the tissue cavity marker to the tissue cavity and an expanded state for residence within the tissue cavity, wherein injection of a fill material into the internal volume of the expandable pouch through the fill aperture causes the expandable pouch to transition from the compressed state to the expanded state, wherein the exterior perimeter and fill aperture of the expandable pouch are configured to retain the fill material within the internal volume while in the expanded state, and wherein a diameter of the expandable pouch in the expanded state is at least about 1.5 times larger and not more than about 3.5 times larger than a diameter of the delivery path.

2. The tissue cavity marker of claim 1, wherein the at least one radiopaque marker is coupled to the exterior perimeter of the expandable pouch.

3. The tissue cavity marker of claim 1, wherein the at least one radiopaque marker is retained within the expandable pouch.

4. The tissue cavity marker of claim 1, wherein the at least one radiopaque marker comprises titanium or nonferromagnetic stainless steel.

5. The tissue cavity marker of claim 1, wherein the expandable pouch comprises a bioabsorbable material.

6. The tissue cavity marker of claim 1, wherein the at least one functional material comprises at least one of an anti-infection material, a hemostasis material, or an anti-migration material.

7. The tissue cavity marker of claim 1, wherein the diameter of the expandable pouch in the expanded state is between about 12 millimeters (mm) and about 20 mm.

8. The tissue cavity marker of claim 7, wherein the diameter of the delivery path is between about 6 mm and about 8 mm.

9. The tissue cavity marker of claim 8, wherein a diameter of the expandable pouch in the compressed state is less than about 7.5 mm.

10. The tissue cavity marker of claim 1, wherein at least one dimension of the tissue cavity marker in the expanded state is approximately equal to or greater than a dimension of the tissue cavity.

11. The tissue cavity marker of claim 1, further comprising a scaffold structure arranged within the internal volume of the expandable pouch in the expanded state.

12. The tissue cavity marker of claim 11, wherein the scaffold structure is arranged within the internal volume of the expandable pouch in the compressed state.

13. The tissue cavity marker of claim 12, wherein the scaffold structure transitions between a compressed state and an expanded state along with the expandable pouch.

14. The tissue cavity marker of claim 11, wherein the scaffold structure is injected into the expandable structure before or with the fill material.

15. The tissue cavity marker of claim 1, wherein the fill aperture comprises a one-way valve to allow the fill material to be injected and retained within the internal volume of the expandable pouch.

16. A tissue cavity marking system for delivering a tissue cavity marker to a tissue cavity via a delivery path between a minimally invasive surgical incision and the tissue cavity, the system comprising:
   a deployment device comprising a control mechanism at a proximal end and a tissue cavity marker aperture at a distal end, the control mechanism operable in use to deploy a tissue cavity marker from the tissue cavity marker aperture; and
   at least one tissue cavity marker comprising:
      an expandable pouch comprising:
         at least one functional material;
         an exterior perimeter that defines an internal volume;
         a fill aperture on the exterior perimeter; and
         at least one radiopaque marker,
         the expandable pouch having a compressed state for temporary arrangement in the tissue cavity marker aperture and an expanded state for residence within the tissue cavity, wherein injection of a fill material into the internal volume of the expandable pouch causes the expandable pouch to transition from the compressed state to the expanded state within the tissue cavity, wherein the exterior perimeter and fill aperture of the expandable pouch are configured to retain the fill material within the internal volume while in the expanded state, and wherein a diameter of the expandable pouch in the expanded state is at least about 1.5 times larger and not more than about 3.5 times larger than a diameter of the distal end of the deployment device.

17. The tissue cavity marking system of claim 16, wherein the deployment device further comprises at least one chamber for the fill material, and wherein the control mechanism is operable in use to enable selective injection of the fill material from the at least one chamber to the expandable pouch.

18. The tissue cavity marking system of claim 17, wherein the distal end of the deployment device comprises a first lumen and a second lumen, wherein the first lumen comprises the tissue cavity marker aperture and the second lumen is fluidly coupled with the at least one chamber.

19. The tissue cavity marking system of claim 17, wherein the fill material is preloaded in the at least one chamber.

20. The tissue cavity marking system of claim 16, wherein one of the at least one tissue cavity markers is preloaded in the tissue cavity marker aperture.

21. The tissue cavity marking system of claim 20, further comprising a sterile package in which the deployment device is sealed.

22. The tissue cavity marking system of claim 16, wherein a diameter of the distal end of the deployment device is less than a length of the minimally invasive surgical incision.

23. The tissue cavity marking system of claim 22, wherein the length of the minimally invasive surgical incision is less than 1 centimeter (cm).

24. The tissue cavity marking system of claim 16, wherein the at least one functional material comprises at least one of an anti-infection material, a hemostasis material, or an anti-migration material.

25. The tissue cavity marking system of claim 16, wherein the diameter of the expandable pouch in the expanded state is between about 12 millimeters (mm) and about 20 mm.

26. The tissue cavity marking system of claim 25, wherein the diameter of the distal end of the deployment device is between about 6 mm and about 8 mm.

27. The tissue cavity marking system of claim 26, wherein a diameter of the expandable pouch in the compressed state is less than about 7.5 mm.

28. The tissue cavity marking system of claim 16, wherein the at least one tissue cavity marker further comprises a scaffold structure.

29. The tissue cavity marking system of claim 28, wherein the scaffold structure is arranged within the expandable pouch in the compressed state when the at least one tissue cavity marker is temporarily arranged in the tissue cavity marker aperture.

30. The tissue cavity marking system of claim 29, wherein the scaffold structure transitions between a compressed state and an expanded state in the tissue cavity along with the expandable pouch.

31. The tissue cavity marking system of claim 28, wherein the scaffold structure is injected into the expandable structure before or with the fill material by the deployment device.

* * * * *